(12) United States Patent
Levin et al.

(10) Patent No.: US 7,205,447 B2
(45) Date of Patent: Apr. 17, 2007

(54) PROCESS FOR REMOVING ALDEHYDES AND/OR KETONES FROM AN OLEFINIC STREAM

(75) Inventors: Doron Levin, Annadale, NJ (US); James Clark Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 513 days.

(21) Appl. No.: 10/410,720

(22) Filed: Apr. 9, 2003

(65) Prior Publication Data

US 2004/0122275 A1    Jun. 24, 2004

Related U.S. Application Data

(60) Provisional application No. 60/436,161, filed on Dec. 23, 2002.

(51) Int. Cl.
*C07C 1/00* (2006.01)
(52) U.S. Cl. ............... 585/638; 585/639; 585/640
(58) Field of Classification Search ........ 585/638, 585/639, 640, 833, 855
See application file for complete search history.

(56) References Cited

U.S. PATENT DOCUMENTS

| | | | |
|---|---|---|---|
| 4,150,063 A * | 4/1979 | Besozzi et al. ............. 585/443 |
| 4,263,443 A | 4/1981 | White .................. 549/83 |
| 4,374,295 A | 2/1983 | Lee .................. 585/640 |
| 4,587,373 A | 5/1986 | Hsia .................. 585/639 |
| 4,625,050 A | 11/1986 | Current .............. 560/232 |
| 4,912,281 A | 3/1990 | Wu .................. 585/640 |
| 5,095,156 A | 3/1992 | Radlowski et al. ......... 568/905 |
| 5,364,979 A | 11/1994 | Radlowski et al. ......... 568/697 |
| 5,491,273 A | 2/1996 | Santiesteban et al. ....... 585/639 |
| 5,602,289 A * | 2/1997 | van Dijk .................. 585/315 |
| 6,403,854 B1 | 6/2002 | Miller et al. ............... 585/638 |
| 6,559,248 B2 * | 5/2003 | Hendriksen et al. ......... 526/77 |
| 6,838,587 B2 * | 1/2005 | Lattner et al. ............. 585/807 |

FOREIGN PATENT DOCUMENTS

| | | |
|---|---|---|
| DE | 27 20 749 | 11/1978 |
| DE | 32 10 756 | 9/1983 |
| EP | 0 229 994 | 5/1989 |

OTHER PUBLICATIONS

Gines, M.J.L. et al. "*Bifunctional Condensation Reactions of Alcohols on Basic Oxides Modified by Copper and Potassium*", Journal of Catalysis, vol. 176, pp. 155-172 (1998).

Engelen, C.W.R. et al. "*The Conversion of Dimethylether Over Pt/H/ZSM5. A Bifunctional Catalyzed Reaction*", B. Imelik et al (Editors), Catalysis by Acids and Bases, pp. 391-398, Elsevier Science Publishers B.V., Amsterdam (1985).

Nakamura, I. et al. "*Hydrocracking of residual oils with iron supported zeolite containing catalyst*", T. Inui et al. (Editors), New Aspects of Spillover Effect in Catalysis, pp. 77-84, Elsevier Science Publishers B.V., Amsterdam (1993).

Levin, D. et al. "*A Novel Dual Component Catalyst for Methanol Conversion to Light Olefins*", Patent Memorandum No. 2001-CL-135, ExxonMobil Research and Engineering Company, 7 pages (2002).

* cited by examiner

*Primary Examiner*—Glenn Caldarola
*Assistant Examiner*—In Suk Bullock
(74) *Attorney, Agent, or Firm*—M. Michalerya

(57) ABSTRACT

The present invention provides a process for removing an oxygenate impurity selected from aldehyde and/or ketone, from an olefinic product stream. A product stream is contacted with a metal oxide-containing catalyst in the presence of a $C_1$ to $C_6$ alcohol under conditions sufficient to convert the oxygenate impurity to an olefin and/or oxygenate of higher carbon number than the aldehyde and/or ketone. The aldehyde can be $C_2$ to $C_5$ aldehyde and the ketone can be $C_3$ to $C_6$ ketone. The metal oxide-containing catalyst typically comprises an oxide of at least one metal selected from the group consisting of Group 2 metals, Group 3 metals (including Lanthanide and Actinide series metals), and Group 4 metals.

16 Claims, No Drawings

PROCESS FOR REMOVING ALDEHYDES AND/OR KETONES FROM AN OLEFINIC STREAM

CROSS REFERENCE TO RELATED APPLICATIONS

The present application claims the benefit of U.S. Provisional Application No. 60/436,161 filed Dec. 23, 2002, the entire content of which is incorporated herein by reference.

FIELD

The present invention relates to a method for removing aldehyde and/or ketone oxygenates from an olefinic stream by contacting the stream with a catalyst in the presence of an alcohol under conditions sufficient to convert the aldehyde and/or ketone oxygenates in the presence of a catalyst to higher boiling compounds which are more readily separable from the stream, and then removing the higher boiling compounds from the stream.

BACKGROUND

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol and ethanol, dimethyl ether (DME), methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins generates by-products whose presence is undesirable for subsequent applications of the collected olefins. Methanol conversion can be carried out over small pore molecular sieves having a chabazite structure and, more specifically, silicoaluminophosphates such as SAPO-34. These small pore molecular sieves are very efficient in converting methanol to light olefins, primarily ethylene and propylene. However, as a by-product of the methanol conversion chemistry, small amounts of oxygenates are produced. Typically, aldehydes and/or ketones, as well as ethers can be present as by-products. The presence of $C_2$ to $C_5$ aldehydes and $C_3$ to $C_6$ ketones can lead to formation of undesired compounds such as red oils, which create problems during subsequent processing. Accordingly, these oxygenates need to be removed from the olefinic product streams to meet product quality requirements. Even though these oxygenates may be present in only small quantities, a significant investment of capital is needed for their removal by conventional separation technology, e.g. distillation, owing to their nearness in boiling point to the boiling points of desired olefin products. Accordingly, it would be desirable to provide a means for eliminating at least some of these oxygenates by reacting them over a suitable catalyst with a reactant to produce less troublesome components, e.g., higher boiling components.

Methods for recovering and recycling dimethyl ether from a methanol-to-chemical conversion reaction using a dimethyl ether absorber tower are disclosed in U.S. Pat. No. 4,587,373 to Hsia.

Stud. Surf. Sci. Catal. (1985), 20 (Catl. Acids Bases), 391–8, discusses low temperature conversion of dimethyl ether over Pt/H-ZSM-5 in the presence of hydrogen by a bifunctional catalyzed reaction.

Stud. Surf. Sci. Catal. (1993), 77 discusses hydrogenation of oxygenates such as dimethyl ether over a $Ni/Al_2O_3$ catalyst to form methane.

U.S. Pat. No. 5,491,273 to Chang et al. discloses conversion of lower aliphatic alcohols and corresponding ethers to linear olefins over large crystal zeolites, e.g., ZSM-35 containing a hydrogenation component of Group VIA and Group VIIIA metals.

DE3210756 discloses a process for converting methanol and/or dimethyl ether feed to olefins by reacting the feed over a pentasil type zeolite catalyst, separating $C_2$–$C_4$ olefins, methane and water from the reaction product and catalytically hydrogenating the remaining components over Co—Mo supported on alumina, optionally preceded by hydrogenation over a Group 8 noble metal for polyunsaturated, non-aromatic compounds.

U.S. Pat. No. 4,912,281 to Wu discloses converting methanol or methyl ether to light olefins in the presence of hydrogen and ZSM-45 which is highly selective to $C_2$–$C_4$ olefins, especially ethylene.

DE2720749 discloses converting lower aliphatic ethers to hydrocarbons in the presence of amorphous, non-acid-activated Al silicate.

U.S. Pat. No. 4,625,050 to Current discloses the use of carbonylation to convert dimethyl ether to methyl acetate and ethanol (as well as minor amounts of methyl formate and propanol) over hydrogen and CO in the presence of heterogeneous NiMo catalyst on an alumina support.

EP-229994 discloses the removal of dimethyl ether as an impurity (1–500 wppm) of olefinic hydrocarbon feedstock by passing the feedstock through an adsorbent mass of crystalline zeolite molecular sieve having the crystal structure of faujasite at 0–60° C. and 0.15–500 psia to selectively absorb dimethyl ether.

"Bifunctional Condensation Reactions of Alcohols on Basic Oxides Modified by Copper and Potassium", M. J. L. Gines and E. Iglesia, *J. Catal.*, 176, 155–172 (1998) discloses alcohol dehydrogenation and condensation reactions involved in chain growth pathways on $Cu/MgCeO_x$ which lead to formation of isobutanol with high selectivity via reactions of higher alcohols with methanol-derived $C_1$ species in reaction steps.

Given the difficulties presented in removing oxygenate by-products of oxygenates to olefins processes such as aldehydes and/or ketones, as well as ethers, it would be advantageous to remove at least one or more of these by-products with techniques that do not require dedicated equipment for superfractionation, water washing, etc.

SUMMARY

In one aspect, the present invention relates to a process for at least partially removing from a product stream an oxygenate impurity selected from aldehyde and/or ketone, the product stream comprising one or more of a $C_2$ to $C_6$ olefin(s). The process comprises: contacting the product stream with a metal oxide-containing catalyst in the presence of a $C_1$ to $C_6$ alcohol under conditions sufficient to convert the oxygenate impurity selected from aldehyde and/or ketone to an olefin and/or oxygenate of higher carbon number than the aldehyde and/or ketone. In one embodiment of this aspect of the invention, the aldehyde is selected from $C_2$ to $C_5$ aldehyde and the ketone is selected from $C_3$ to $C_6$ ketone. The metal oxide-containing catalyst comprises an oxide of a metal selected from the group consisting of Group 2 metals, Group 3 metals (including Lanthanide and Actinide series metals) and Group 4 metals. In such an embodiment, the catalyst may include two or more metals from the same group of metals. For example, the metal oxide-containing catalyst can comprise an oxide of a metal selected from the group consisting of Group 3 metals and Lanthanide series metals.

In another embodiment, the $C_1$ to $C_6$ alcohol is methanol and the aldehyde is acetaldehyde.

In still another embodiment, the metal oxide-containing catalyst comprises an oxide of a metal selected from the group consisting of Mg, Ca, Sr, Ba and Ra.

In yet another embodiment of this aspect, the metal oxide-containing catalyst comprises an oxide of a metal selected from the group consisting of Sc, Y, La, Ce, Pr, Nd, Pm, Sm, Eu, Gd, Tb, Dy, Ho, Er, Tm, Yb, Lu, Ac, Th, Pa, U, Np, Pu, Am, Cm, Bk, Cf, Es, Fm, Md, No, and Lr, preferably Sc, Y, La, and Ce, with Y especially preferred.

In still yet another embodiment, the metal oxide-containing catalyst comprises an oxide of a metal selected from the group consisting of Ti, Zr, and Hf.

In another embodiment, the metal oxide-containing catalyst comprises an oxide of Zr.

In still another embodiment of this aspect, the metal oxide-containing catalyst comprises an oxide of a metal selected from the group consisting of Group 2 metals, Group 3 metals and Group 4 metals, say, an oxide of a metal selected from the group consisting of Group 2 metals and Group 3 metals, e.g., lanthanum oxide and magnesium oxide.

In yet another embodiment, the metal oxide-containing catalyst comprises an oxide of a metal selected from the group consisting of Group 3 metals and Group 4 metals, say, lanthanum oxide and zirconium oxide.

In yet still another embodiment, the metal oxide-containing catalyst comprises an oxide of a metal selected from the group consisting of Group 2 metals and Group 4 metals, e.g., calcium oxide and zirconium oxide.

In another embodiment of this aspect of the invention, the product stream prior to said contacting comprises at least about 0.05 wt % aldehyde and/or at least about 0.05 wt % ketone, based on total weight of the product stream prior to the contacting.

In still another embodiment, the product stream after said contacting contains less than about 0.025 wt % aldehyde and/or less than about 0.025 wt % ketone, based on total weight of the product stream after said contacting.

In yet another embodiment, the prime olefin ($C_2$ to $C_3$) content of the product stream after the contacting based on the total weight of the product stream after contacting is reduced by less than about 3 wt % as compared to the prime olefin content of the product stream before the contacting based on total weight of the product stream before the contacting.

In yet still another embodiment, the prime olefin content of the product stream after the contacting based on the total weight of the product stream after contacting is reduced by less than about 2 wt % as compared to the prime olefin content of said product stream before the contacting based on total weight of the product stream before the contacting.

In another embodiment, the contacting provides an oxygenate impurity-depleted stream which comprises no greater than about 250 wppm of aldehyde and/or ketone based on total weight of the impurity-depleted stream.

In still another embodiment of this aspect, the contacting provides an oxygenate impurity-depleted stream which comprises no greater than about 50 wppm acetaldehyde based on the total weight of the impurity-depleted stream.

In yet another embodiment, the contacting is carried out at temperatures ranging from about 25° to about 750° C., (from about 77° to about 1382° F.) and a total pressure ranging from about 100 to about 3500 kPaa (from about 14.5 to about 508 psia), e.g., temperatures ranging from about 100° to about 550° C., (from about 212° to about 1022° F.) and a total pressure ranging from about 207 to about 827 kPaa (from about 30 to about 120 psia).

In one embodiment of this aspect of the invention, no greater than about 10 wt %, say, no greater than about 5 wt %, of the $C_2$ to $C_6$ olefin(s) is converted by the contacting step.

In another embodiment, the contacting is carried out in the absence of hydrogen.

In still another embodiment, the contacting is carried out in the presence of hydrogen.

In yet another embodiment of this aspect, at least about 20%, say, at least about 50%, e.g., at least about 80%, of the aldehyde and/or ketone is converted during the contacting step.

In another aspect, the present invention relates to a process for converting oxygenates to olefins which comprises at least one of: 1) exposing an oxygenate-containing feed with an olefin generation catalyst under conditions sufficient to provide a first product stream which contains water, carbon dioxide, methane, ethane, $C_2$ to $C_6$ olefins, and oxygenates comprising i) alcohol and ii) aldehyde and/or ketone; 2) compressing and cooling the first product stream in at least one stage to provide a compressed and cooled product stream; 3) separating water from the compressed and cooled product stream in a separator column from which a water-rich stream is taken as bottoms and a water-depleted product stream is taken as overhead; 4) removing carbon-dioxide from the water-depleted product stream in a caustic scrubber from which a carbon dioxide-rich stream is taken as bottoms and a carbon dioxide-depleted product stream is taken as overhead; drying the carbon dioxide-depleted product stream in a dryer to provide a dried product stream; 6) demethanizing the dried product stream in a demethanizer from which a methane-rich stream is taken as overhead and a methane-depleted product stream is taken as bottoms; and 7) deethanizing the methane-depleted product stream in a deethanizer from which a $C_2$– product stream is taken as overhead and a $C_3$+ product stream is taken as bottoms; and which process further comprises contacting at least one of the aforementioned product streams with a metal oxide-containing catalyst in the presence of a $C_1$ to $C_6$ alcohol under conditions sufficient to convert the oxygenate impurity selected from aldehyde and/or ketone to an olefin and/or oxygenate of higher carbon number than the aldehyde and/or ketone.

In one embodiment of this aspect, the contacting is carried out with the first product stream.

In another embodiment, the contacting is carried out with the compressed and cooled product stream.

In still another embodiment, the contacting is carried out with the water-depleted product stream.

In yet another embodiment, the contacting is carried out with the carbon dioxide-depleted product stream.

In still yet another embodiment, the contacting is carried out with the dried product stream.

In another embodiment of this aspect of the invention, the contacting is carried out with the methane-depleted product stream.

In still another embodiment, the contacting is carried out with the $C_2$- product stream.

In yet another embodiment, the contacting is carried out with the $C_3$+ product stream.

In still yet another aspect, the present invention relates to a process for converting oxygenates into one or more olefins(s) in a reactor in the presence of a molecular sieve catalyst. The process comprises the steps of: (a) withdrawing a product stream from the reactor, the product stream comprising one or more of a $C_2$ to $C_6$ olefin(s), a $C_1$ to $C_6$ alcohol, and a mixture of impurities; and (b) contacting the product stream with a metal oxide-containing catalyst under conditions sufficient to convert at least some of the mixture of impurities into an olefin and/or oxygenate having a higher number of carbon atoms than one or more of the mixture of impurities.

In one embodiment of this aspect, the mixture of impurities comprises aldehyde and/or ketone.

In another embodiment, the mixture of impurities comprises aldehyde and ketone.

DETAILED DESCRIPTION

Molecular Sieves and Catalysts Thereof for Use in OTO Conversion

Molecular sieves suited to use for converting oxygenates to olefins (OTO) have various chemical, physical, and framework characteristics. Molecular sieves have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof, and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Crystalline molecular sieve materials all have 3-dimensional, four-connected framework structure of corner-sharing $[TO_4]$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12- ring structures or larger and an average pore size in the range of from about 3 Å to 15 Å. In the most preferred embodiment, the molecular sieves utilized in the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, R. Szostak, *Handbook of Molecular Sieves,* Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group 1 of the Periodic Table of Elements, an alkaline earth metal of Group 2 of the Periodic Table of Elements, a rare earth metal of Group 3, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups 4, 5, 6, 7, 8, 9, 10, 11, and 12 of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group 1, 2, 3, 4, 5, 6, 7, 8, 9, 10, 11, 12, 13, 14 and Lanthanide's of the Periodic Table of Elements, preferably M is selected from one of the group consisting of Co, Cr, Cu, Fe, Ga, Ge, Mg, Mn, Ni, Sn, Ti, Zn and Zr.

In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves useful as catalysts in oxygenates to olefins processes include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized by techniques known to those skilled in the art and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins Process

In a preferred embodiment of an oxygenate to olefins process, the feedstock contains one or more oxygenates, more specifically, one or more organic compound(s) containing at least one oxygen atom. In the most preferred embodiment, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in an oxygenate to olefins process include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

The most preferred process for converting a feedstock into olefin(s) is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as prime olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 85 weight percent.

The process for converting a feedstock, especially a feedstock containing one or more oxygenates, in the presence of a molecular sieve catalyst composition, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In a preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kpaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether to olefin(s) is in the range of from about 20 $hr^{-1}$ to about 300 $hr^{-1}$.

Under these process conditions, the feedstock entering the reactor system is preferably converted, partially or fully, in the first reactor zone into a gaseous effluent that enters the disengaging vessel along with a coked molecular sieve catalyst composition. In a preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone.

The coked molecular sieve catalyst composition may be withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, most preferably air, under general regeneration conditions of temperature, pressure and residence time as is well known to those skilled in the art.

The gaseous effluent from the OTO reactor is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Treatment of Olefinic Streams Containing Oxygenates

Olefinic Streams Containing Oxygenates

The streams contemplated for treatment by the present invention comprise at least one $C_x$ olefin wherein x is an integer ranging from 2 to 6, as well as oxygenates selected from the group consisting of aldehydes and ketones. Typically such aldehydes are selected from the group consisting of formaldehyde, acetaldehyde, propionaldehyde, n-butyraldehyde, isobutyraldehyde, crotonaldehyde, valeraldehyde, isovaleraldehyde, hexanal and heptanal. $C_2$ to $C_6$ aldehydes, say, $C_2$ to $C_5$ aldehydes, are often constituents of the streams that can be processed by the present invention.

In one embodiment, suitable streams for treatment by the present invention comprise ketones. Typically such ketones include aromatic ketones such as benzophenone, alkylaromatic ketones such as acetophenone, alkyl ketones such as acetone, methyl ethyl ketone, ethyl ketone, n-propyl ketone, isopropyl ketone, n-propyl isopropyl ketone, methyl n-propyl ketone, methyl isopropyl ketone, methyl n-butyl ketone, methyl isobutyl ketone, methyl tert-butyl ketone, ethyl n-propyl ketone, ethyl isopropyl ketone, n-butyl ketone, isobutyl ketone, tert-butyl ketone, ethyl n-butyl ketone, ethyl isobutyl ketone, ethyl tert-butyl ketone, etc. In one embodiment, the ketone is selected from $C_3$ to $C_6$ alkyl ketones.

In one embodiment, the streams for treatment by the present invention comprises an alcohol, typically a $C_1$ to $C_6$ alcohol, e.g., an alkyl alcohol, say, methanol. Such alcohol is often present as an unreacted oxygenate reactant which was fed to an oxygenates to olefin process. The alcohol is suitable for catalytically reacting with the oxygenate impurity selected from aldehyde and/or ketone to provide an oxygenated molecule of higher carbon number than the aldehyde and/or ketone. In an alternative embodiment, the alcohol is separately added to the feed for subsequent catalytic reacting with the oxygenate impurity. The molar ratio of alcohol to oxygenate impurity selected from aldehyde and/or ketone ranges from about 1000:1 to about 1 0:1, typically from about 100:1 to about 5:1, say, from about 50:1 to about 1:1. In an embodiment wherein the feed itself comprises alcohol, the feed contains anywhere from 10 to about 99.9 wt % alcohol. Typically, such product streams treated in accordance with the present invention are prepared by steam cracking of alkanes or derived from oxygenated feedstocks as described above for oxygenate to olefins processes.

The conversion of ketones over basic catalyst materials in the presence of an alcohol can be quite complex. Without wishing to be bound by theory, it is noted that reaction mechanisms based on literature investigations of vapor phase reaction between acetone and methanol include several types. Type 1 relates to the methylation of acetone followed by dehydrogenation to form methyl vinyl ketone (MVK). Type 2 relates to the Meerwein-Ponndorf-Verley dehydration to form propylene and formaldehyde. Type 3 relates to the condensation of acetone followed by further decomposition to form isobutylene. The balance between these three mechanisms is dependent on the nature of the catalyst and reaction conditions. Typically, catalysts of the present invention are selected that would favor Types 2 and 3, inasmuch as the end products of these chemistries are mostly olefins.

Conversion chemistry of aldehydes in the presence of alcohol over basic oxides is very complex. While not wishing to be bound by theory, it is believed that various mechanistic pathways can be involved that are dependent on the nature of the basic oxides. For example, a possible mechanism contributing to oxygenate removal is exemplified by the reaction of acetaldehyde with methanol to form propionaldehyde, which reacts further with methanol to form isobutyraldehyde, which may then be hydrogenated to isobutyl alcohol. In regard to formation of isobutyl alcohol from acetaldehyde, a separate hydrogenation step is generally not required to convert isobutyraldehyde to isobutyl alcohol. It is believed there are sufficient hydrogen transfer reactions taking place to catalyze this chemistry simultaneously to the condensation reactions occurring with the aldehydes and methanol. The isobutyl alcohol can then be easily removed, or recycled back to an oxygenates to olefin reactor where it can undergo dehydration to isobutene that is recoverable with $C_4$ olefins. Of course, such a mechanism can also be used to directly remove propionaldehyde impurities from a product stream. A proposed reaction pathway for removing acetaldehyde in the presence of methanol is set out below:

$$C_2H_4O + CH_3OH \rightarrow C_3H_6O + H_2O$$

$$C_3H_6O + CH_3OH \rightarrow C_4H_8O + H_2O$$

$$C_4H_8O + H_2 \rightarrow C_4H_9OH$$

$$C_4H_9O - H_2O \rightarrow C_4H_8$$

The chemistry of Reactions (1) and (2) has been confirmed by $^{13}C$—labeled methanol studies by Gines and Iglesia, "Bifunctional Condensation Reactions of Alcohols on Basic Oxides Modified by Copper and Potassium," Journal of Catalysis 176, 155–172 (1998). Isobutyraldehyde is a preferred end-product of this chemistry inasmuch as it lacks the two α-hydrogens required for subsequent chain growth.

In addition, the product stream treated in accordance with the present invention may contain additional oxygenate components, e.g., ethers. Representative ethers are those selected from at least one of dimethyl ether, diethyl ether, di-n-propyl ether, diisopropyl ether, methylethyl ether, methyl-n-propyl ether, methylisopropyl ether, ethyl-n-propyl ether, ethylisopropyl ether and n-propylisopropyl ether.

Streams contemplated for processing by the present invention can vary greatly in the amount of oxygenate present. Typically such streams comprise at least 1 ppm oxygenates, say, at least about 10, at least about 50, at least about 100, at least about 1000, at least about 10000, or even at least about 25000 ppm total oxygenates. In certain embodiments of the invention, such streams contain up to about 30000 ppm, say, up to about 50000 ppm oxygenates, e.g., alcohol, e.g., methanol, and about 100 to about 10000 ppm aldehyde and/or ketone.

The process of the present invention is particularly useful in treating ethylene- and/or propylene-containing product streams that contain oxygenate impurities. Typically, such product streams range from about 5 to about 95 wt % ethylene and/or propylene, say, from about 15 to about 90 wt % ethylene and/or propylene, e.g., from about 25 to about 85 wt % ethylene and/or propylene. Oxygenate impurities may be present in the same amounts as described above for other product streams.

Aldehyde and/or Ketone Conversion Catalyst

Generally, a selective catalyst exhibiting aldehyde and/or ketone conversion properties without substantially converting olefinic components is employed in the present invention. The present invention utilizes a metal oxide-containing catalyst comprising an oxide of a metal selected from the group consisting of Group 2 metals, Group 3 metals (including Lanthanide and Actinide series metals) and Group 4 metals, say, an oxide of a metal selected from the group consisting of Mg, Ca, Sr, Ba and Ra, and/or an oxide of a metal selected from the group consisting of Sc, Y, La, Ce, Pr, Nd, Pm, Sm, Eu, Gd, Tb, Dy, Ho, Er, Tm, Yb, Lu, Ac, Th, Pa, U, Np, Pu, Am, Cm, Bk, Cf, Es, Fm, Md, No, and Lr, and/or an oxide of a metal selected from the group consisting of Ti, Zr, and Hf.

In one embodiment, it is preferred to utilize a mixed metal oxide catalyst comprising at least two or more metal oxides, preferably selected from oxides of Group 2, Group 3 (including Lanthanide and Actinide series metals) and Group 4 metals. The metal oxides useful in the invention are combinable in many ways to form the mixed metal oxides. In an embodiment, the metal oxides are mixed together in a slurry or hydrated state or in a substantially dry or dried state, preferably the metal oxides are contacted in a hydrated state.

In a preferred embodiment, the mixed metal oxides can be considered as having atomic level mixing of the Group 2, Group 3, and/or Group 4 metals within the oxide, in which the atomic level mixing is achieved during synthesis of the mixed metal oxide.

The mixed metal oxides of the invention are prepared using a variety of methods. It is preferable that the mixed metal oxide is made from metal oxide precursors, such as metal salts, preferably a Group 2 metal salt precursor, a Group 3 metal salt precursor, and/or a Group 4 metal salt precursor. Other suitable sources of the metal oxides include compounds that form these metal oxides during calcination, such as oxychlorides and nitrates. Alkoxides are also sources of the metal oxides, for example zirconium n-propoxide.

In one embodiment, the metal oxide is hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of hydrated metal oxide in the liquid medium, for example, by the action of refluxing liquid and/or stirring, promotes the effective interaction of the hydrated oxide with the liquid medium. The duration of the contact of the hydrated oxide with the liquid medium is preferably at least about 1 hour, preferably at least about 8 hours. The liquid medium for this treatment preferably has a pH of about 7 or greater, preferably about 9 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In one embodiment, where the metal oxide catalyst of this invention consists of two or more oxides selected from Groups 2, 3, and 4, the mixed metal oxide may be prepared by impregnation of a precursor to a second oxide onto a preformed oxide. In an alternative embodiment, the first formed oxide may be hydrothermally treated prior to impregnation. For example, a Group 3/Group 4 mixed metal oxide can be prepared by impregnating a hydrothermally treated hydrated oxide of the Group 4 metal with an aqueous solution containing an ion of the Group 3 metal, followed by drying. In a preferred embodiment, the Group 3 metal is lanthanum or yttrium. The resulting material is then calcined, preferably in an oxidizing atmosphere, at a temperature of at least about 400° C., preferably at least about 500° C., and more preferably from about 600° C. to about 900° C., and most preferably from about 650° C. to about 800° C. The calcination time may be up to 48 hours, preferably for about 0.5 to about 24 hours, and more preferably for about 1 to about 10 hours. In a most preferred embodiment, calcination is carried out at about 700° C. for about 1 to about 3 hours.

In yet another embodiment, where the metal oxide catalyst of this invention consists of two or more oxides selected from Groups 2, 3, and 4, the mixed metal oxide may be prepared by combining a first liquid solution comprising a source of at least one of the Group 2, 3, or 4 metals with a second liquid solution comprising a source of an ion of at least one other Group 2, 3, or 4 metal. This combination of two solutions takes place under conditions sufficient to cause co-precipitation of the mixed oxide material as a solid from the liquid medium. Alternatively, the sources of the all the anions of the Group 2, 3, and/or 4 metal oxides may be combined in a single solution. This solution may then be subjected to conditions sufficient to cause co-precipitation of the solid mixed oxide material, such as by the addition of a precipitating reagent to the solution. For example, the precipitating agent(s) preferably is a base such as sodium hydroxide or ammonium hydroxide. Water is a preferred solvent for these solutions. The temperature at which the liquid medium(s) is maintained during the co-precipitation is preferably less than about 200° C., preferably in the range of from about 0° C. to about 200° C. This liquid medium(s) is preferably maintained at an ambient temperature, for example room temperature or the liquid is cooled or heated. A particular range of temperatures for co-precipitation is from about 20° C. to about 100° C. The resulting gel is preferably then hydrothermally treated at temperatures of at least about 80° C., preferably at least about 100° C. The hydrothermal treatment typically takes place in a sealed vessel at greater than atmospheric pressure. The gel, in one embodiment, is hydrothermally treated for up to about 10 days, preferably up to about 5 days, most preferably up to about 3 days. The resulting material is then recovered, for example by filtration or centrifugation, and washed and dried. The resulting material is preferably then calcined, preferably in an oxidizing atmosphere, at a temperature of at least about 400° C., preferably at least about 500° C., and more preferably from about 600° C. to about 900° C., and most preferably from about 650° C. to about 800° C. The calcination time is preferably up to 48 hours, preferably for about 0.5 to 24 hours, and more preferably for about 1.0 to 10 hours. In a most preferred embodiment, calcination is carried out at about 700° C. for about 1 to about 3 hours.

In an alternative embodiment, such catalysts comprise an inorganic oxide support, e.g., one comprising at least one element selected from the group consisting of silica, alumina, aluminophosphate, and clay. Preferably, the inorganic oxide comprises alumina.

The foregoing catalysts employed in converting oxygenate impurities can be deactivated during use and can be at least partially regenerated in accordance with the techniques described above for coked oxygenate conversion catalysts, as well as any other suitable regeneration technique known to those skilled in the art.

Oxygenate Conversion Reactors

Suitable oxygenate conversion reactors for converting olefinic streams containing oxygenate impurities include those described above which are taught above for the purpose of converting a feedstock, especially a feedstock containing one or more oxygenates to olefin(s), in the presence of a molecular sieve catalyst composition. Other suitable conversion reactors include fixed bed reactors, fluidized bed reactors, and continuous fluidized bed reactors. Preferably, the conversion reactor for the oxygenate removal process of this invention is a fixed bed reactor.

Oxygenate Conversion Conditions

In one aspect, the present invention utilizes oxygenate conversion conditions which are sufficient to convert an aldehyde and/or ketone oxygenate impurity in the treated stream to an olefin and/or oxygenate of higher carbon number than said aldehyde and/or ketone.

The conversion temperature employed in the conversion of oxygenate impurities, specifically within the reactor system, is in the range of from about 25° C. to about 1000° C., preferably from about 100° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion of oxygenate impurities in accordance with the present invention, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 200 kPaa to about 800 kPaa.

The weight hourly space velocity (WHSV), particularly in a process for converting a feedstock containing one or more oxygenate impurities in the presence of a catalyst within a reaction zone, is defined as the total weight of the feedstock excluding any diluents to the reaction zone per hour per weight of the catalyst in the reaction zone.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and acetaldehyde is in the range of from about 20 $hr^{-1}$ to about 300 $hr^{-1}$.

Typically, these conditions are sufficient to provide conversion of aldehyde and/or ketone oxygenate without substantially converting olefins present in the stream being treated. By "substantially converting" is meant that no greater than about 5 wt %, no greater than about 3 wt %, or even no greater than about 2 wt % of $C_2$ to $C_6$ olefin is converted, singly or in the aggregate. Moreover, these conditions can include the presence or absence of hydrogen depending on the stream being treated and the desired product resulting from conversion of oxygenate impurity.

In the present invention, wherein higher boiling compounds are produced, aldehyde and/or ketone oxygenate impurity conversion can be carried out in the liquid phase. Suitable liquid phase conditions comprise a temperature ranging from about 20° C. to about 100° C., total pressures ranging from about 1140 kPaa to about 4240 kPaa, and LHSV (liquid hourly space velocity) ranging from about 0.1 to about 100.

Alternatively, the converting of aldehyde and/or ketone oxygenate impurities can be carried out in the vapor phase and comprises a temperature ranging from about 25° C. to about 750° C., total pressures ranging from about 7 kpaa to about 3500 kPaa, and GHSV (gas hourly space velocity) ranging from about 10 to about 500,000, preferably comprising a temperature ranging from about 100° to about 600° C., total pressures ranging from about 200 kPaa to about 1480 kPaa, and GHSV ranging from about 100 to about 20,000.

Typically, conversion of aldehyde and/or ketone oxygenate impurities in a treated stream according to the present invention, can be at least about 10%, at least about 50%, at least about 90%, at least about 95%, or even at least about 99%, especially for acetaldehyde conversion.

Separation Methods

Various conventional separation methods known in the art are suitable for separating at least some of the higher boiling oxygenates made by converting aldehyde and/or ketone impurities in the presence of olefin, in accordance with the present invention.

In one aspect of the invention, such separation is carried out by utilizing differences in volatility, e.g., boiling point, between olefins and the conversion products of oxygenate impurities. Exemplary of such methods include fractionation, e.g., with a distillation column, or the use of a vapor-liquid disengaging drum.

In another aspect of the invention, differences in solubility between olefins and the conversion products of oxygenate impurities in aqueous and/or non-aqueous solvents can be relied upon to effect separation, e.g., solvent extraction.

In yet another aspect of the invention, differences in molecular size, shape, polarity, etc. are utilized to effect the desired separation, e.g., membrane separation techniques.

Oxygenate-Depleted Treated Streams

A primary effect of the separation step of the present invention is to provide an oxygenate-depleted stream. One embodiment of the present invention provides an oxygenate impurity-depleted stream which comprises no greater than about 250 ppm, no greater than about 100 ppm, or even no greater-than about 50 ppm aldehyde and/or ketone oxygenate, e.g., acetaldehyde.

The following examples illustrate, but do not limit, the present invention.

EXAMPLES

Example 1 describes the synthesis of the SAPO-34 sieve used for testing. Example 2 describes the formulation of the SAPO-34 sieve. Examples 3 through 6 describe the synthesis of the metal oxide catalysts. Examples 7 though 11 describe the performance of the catalyst for aldehyde removal and provide base case comparisons.

All catalytic or conversion data presented were obtained using a microflow reactor. The microflow reactor consists of a stainless steel reactor (¼ inch (0.64 cm) outer diameter) located in a furnace to which vaporized methanol is fed. The reactor is maintained at a temperature of 475° C. and a pressure of 25 psig (172.4 kPag.) The flow rate of the methanol is such that the flow rate of methanol on weight basis per gram of molecular sieve, also known as the weight hourly space velocity (WHSV) was 100 h$^{-1}$. Product gases exiting the reactor were collected and analyzed using gas chromatography.

The catalyst load of molecular sieve was 40 mg and the bed was diluted with quartz to minimize hot spots in the reactor. To simulate an oxygenate removal bed downstream of the reactor, a catalyst load of 10 mg of the metal oxide, diluted with 5 mg of inert quartz was placed below the molecular sieve bed. For the base case comparison of no oxygenate removal bed, a bed of inert quartz was placed below the molecular sieve bed.

Example 1

There are numerous methods well known for making molecular sieves. The following is an example preparation of a molecular sieve, particularly a silicoaluminophosphate molecular sieve, more particularly a SAPO-34, used for testing in these Examples, and referenced as MSA.

The MSA, SAPO-34 molecular sieve, was crystallized in the presence of tetraethyl ammonium hydroxide (R1) and dipropyl amine (R2) as the organic structure directing agents or templating agents. A mixture of the following mole ratio composition was prepared:

$0.2\ SiO_2/Al_2O_3/P_2O_5/0.9\ R1/1.5\ R2/50\ H_2O$.

An amount of Pural SB pseudoboehmite (75% alumina) obtained from Pural Chemie, was mixed with deionised water, to form a slurry. To this slurry was added an amount of phosphoric acid (85%). These additions were made with stirring to form a homogeneous mixture. To this homogeneous mixture Ludox AS40 (40% of $SiO_2$), was added, followed by the addition of R1 with mixing to form a homogeneous mixture. To this homogeneous mixture R2 was added. This homogeneous mixture was then crystallized with agitation in a stainless steel autoclave by heating to 170° C. for 40 hours. This provided a slurry of the crystalline molecular sieve. The crystals were then separated from the mother liquor by filtration.

Example 2

There are a variety of methods for making or formulating a molecular sieve, a matrix material and a binder into a molecular sieve catalyst composition. The following is an example of making a molecular sieve catalyst composition. The crystalline molecular sieve prepared in Example 1 was thoroughly mixed with water to form a molecular sieve slurry (A1). This slurry (A1) was then added to another slurry (A2) of a binder (for example, preferably aluminum chlorhydrol) and water, and was then again mixed thoroughly. As a final step in the formulation process, a matrix material (A3) (for example, a clay material) was then added to the mixture of A1 and A2, mixed well to form a homogeneous mixture (A4). This mixture (A4) was then fed to a drier, preferably a spray drier, under conditions sufficient to produce a formulated molecular sieve catalyst composition composed of particles having the desired size and dryness. The molecular sieve catalyst composition produced was then calcined at an elevated temperature sufficient to further dry and harden the spray dried molecular sieve catalyst composition or formulated molecular sieve catalyst composition. The catalyst composition was then packaged under a dry atmosphere for use, storage or shipment.

Example 3

Fifty grams of $ZrOCl_2.8H_2O$ were dissolved with stirring in 300 ml of distilled water. Another solution containing 4.2 grams of $La(NO_3)_3.6H_2O$ and 300 ml of distilled water was prepared. These two solutions were combined with stirring to form a final mixture. The pH of the final mixture, a slurry, was adjusted to approximately 9 by the addition of concentrated ammonium hydroxide (28.9 grams). This slurry was then put in a polypropylene bottle and placed in a steam box (100° C.) for 72 hours. The resulting product formed was recovered by filtration, washed with excess water, and dried overnight at 85° C. A portion of this resulting product was calcined to 700° C. in flowing air for 3 hours to produce a mixed metal oxide containing a nominal 5 weight percent La based on the final weight of the mixed metal oxide.

Example 4

Fifty grams of $Y(NO_3)_3.6H_2O$ were dissolved with stirring in 500 ml of distilled water. The pH was adjusted to 9 by the addition of concentrated ammonium hydroxide. This slurry was then put in polypropylene bottles and placed in a steam box (100° C.) for 72 hours. The product formed was recovered by filtration, washed with excess water, and dried overnight at 85° C. A portion of this catalyst was calcined to 600° C. in flowing air for 3 hours to produce yttrium oxide ($Y_2O_3$).

Example 5

Five hundred grams of $ZrOCl_2.8H_2O$ and 112 grams of $Ca(NO_3)_2.4H_2O$ were dissolved with stirring in 3000 ml of distilled water. Another solution containing 260 grams of $NH_4OH$ and 3000 ml of distilled water was prepared. These two solutions were combined with stirring. The pH of the final composite was adjusted to approximately 9 by the addition of concentrated ammonium hydroxide (160 grams). This slurry was then put in polypropylene bottles and placed in a steam box (100° C.) for 72 hours. The resulting product formed was recovered by filtration, washed with excess water, and dried overnight at 85° C. A portion of this product was calcined to 700° C. in flowing air for 3 hours to produce a mixed metal oxide containing a nominal 10 weight percent Ca (calcium) based on the final weight of the mixed metal oxide.

Example 6

One thousand grams of $ZrOCl_2.8H_2O$ was dissolved with stirring in 3.0 liters of distilled water. Another solution containing 400 grams of concentrated $NH_4OH$ and 3.0 liters of distilled water was prepared. Both solutions were heated to 60° C. These two heated solutions were combined at the rate of 50 ml/min using a nozzle mixing. The pH of the final composite was adjusted to approximately 9 by the addition of concentrated ammonium hydroxide. This slurry was then put in polypropylene bottles and placed in a steam box (100° C.) for 72 hours. The product formed was recovered by filtration, washed with excess water, and dried overnight at 85° C. A portion of this product was calcined to 700° C. in flowing air for 3 hours to produce a zirconium oxide material.

Example 7

The catalytic performance of the base case catalyst, MSA synthesized in Example 1, formulated with 40% sieve in an alumina binder according to Example 2, was investigated. The results of the run are presented in the TABLE below.

TABLE

| Example | Reactor Bed Composition | Prime Olefin (%) | Acetaldehyde (wt. %) | $C_2^=/C_3^=$ |
|---|---|---|---|---|
| 7 | MSA | 71.6 | 0.096 | 0.82 |
| 8 | MSA (Top) 5% La/ZrO$_2$ (Bottom) | 71.0 | 0.000 | 0.82 |
| 9 | MSA (Top) Y$_2$O$_3$ (Bottom) | 9.8 | 0.000 | 0.81 |
| 10 | MSA (Top) 10% Ca/ZrO$_2$ (Bottom) | 70.8 | 0.000 | 0.81 |
| 11 | MSA (Top) ZrO$_2$ (Bottom) | 71.6 | 0.000 | 0.83 |

| Ex | Reactor Bed Composition | CH$_4$ | $C_2^=$ | $C_2^o$ | $C_3^=$ | $C_3^o$ | $C_4$'s | $C_5$+ |
|---|---|---|---|---|---|---|---|---|
| 7 | MSA | 1.31 | 32.2 | 0.78 | 39.4 | 2.9 | 15.2 | 4.5 |
| 8 | MSA (Top) 5% La/ZrO$_2$ (Bottom) | 1.32 | 32.0 | 0.94 | 39.0 | 3.5 | 14.9 | 4.4 |
| 9 | MSA (Top) Y$_2$O$_3$ (Bottom) | 1.24 | 31.2 | 0.93 | 38.5 | 4.0 | 15.4 | 4.8 |
| 10 | MSA (Top) 10% Ca/ZrO$_2$ (Bottom) | 1.25 | 31.6 | 0.80 | 39.2 | 3.2 | 15.5 | 4.7 |
| 11 | MSA (Top) ZrO$_2$ (Bottom) | 1.29 | 32.4 | 0.86 | 39.2 | 3.3 | 15.2 | 4.1 |

In this TABLE, "Prime Olefin" is the sum of the selectivity to ethylene and propylene. The ratio "$C_2^=/C_3^=$" is the ratio of the ethylene to propylene selectivities weighted over the run. The selectivities for acetaldehyde, methane, ethylene, ethane, propylene, propane, $C_4$'s and $C_5$+'s are average selectivities weighted over the run. Note that the $C_5$+'s consist only of $C_5^1$s, $C_6$'s and $C_7$'s. The selectivities do not sum to 100% in the TABLE because these selectivities have been corrected for coke.

Example 8

To simulate the performance of a reactor containing the catalyst of Example 3 located just downstream of the MTO reactor, a stacked bed configuration was used. Ten milligrams of the catalyst of Example 3 were loaded into the bottom of the reactor. Forty milligrams of the base case catalyst, MSA, formulated according to Example 2, were loaded above the bed of the catalyst of Example 3. The results of the run are presented in the TABLE and show a reduction in acetaldehyde concentration by 100%. Selectivities of the major MTO products have not changed significantly by passage over the Group 4 metal oxide modified by a Group 3 metal oxide of this invention.

Example 9

To simulate the performance of a reactor containing the catalyst of Example 4 located just downstream of the MTO reactor, a stacked bed configuration was used. Ten milligrams of the catalyst of Example 4 were loaded into the bottom of the reactor. Forty milligrams of the base case catalyst, MSA, formulated according to Example 2, were loaded above the bed of the catalyst of Example 4. The results of the run are presented in the TABLE and show a reduction in acetaldehyde concentration by 100%. Selectivities of the major MTO products have not changed significantly by passage over the Group 3 metal oxide of this invention.

Example 10

To simulate the performance of a reactor containing the catalyst of Example 5 located just downstream of the MTO reactor, a stacked bed configuration was used. Ten milligrams of the catalyst of Example 5 were loaded into the bottom of the reactor. Forty milligrams of the base case catalyst, MSA, formulated according to Example 2, were loaded above the bed of the catalyst of Example 5. The results of the run are presented in the TABLE and show a reduction in acetaldehyde concentration by 100%. Selectivities of the major MTO products have not changed significantly by passage over the Group 4 metal oxide modified by a Group 2 metal oxide of this invention.

Example 11

To simulate the performance of a reactor containing the catalyst of Example 6 located just downstream of the MTO reactor, a stacked bed configuration was used. Ten milligrams of the catalyst of Example 6 were loaded into the bottom of the reactor. Forty milligrams of the base case catalyst, MSA, formulated according to Example 2, were loaded above the bed of the catalyst of Example 6. The results of the run are presented in the TABLE and show a reduction in acetaldehyde concentration by 100%. Selectivities of the major MTO products have not changed significantly by passage over the Group 4 metal oxide of this invention.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for converting oxygenates to olefins which comprises at least one of:
   1) exposing an oxygenate-containing feed with an olefin generation catalyst under conditions sufficient to provide a first product stream which contains water, carbon dioxide, methane, ethane, $C_2$ to $C_6$ olefins, and oxygenates comprising i) alcohol and ii) impurities comprising aldehyde and/or ketone;
   2) compressing and cooling said first product stream in at least one stage to provide a compressed and cooled product stream;
   3) separating water from said compressed and cooled product stream in a separator column from which a water-rich stream is taken as bottoms and a water-depleted product stream is taken as overhead;
   4) removing carbon dioxide from said water-depleted product stream in a caustic scrubber from which a carbon dioxide-rich stream is taken as bottoms and a carbon dioxide-depleted product stream is taken as overhead;
   5) drying said carbon dioxide-depleted product stream in a dryer to provide a dried product stream;
   6) demethanizing said dried product stream in a demethanizer from which a methane-rich stream is taken as overhead and a methane-depleted product stream is taken as bottoms; and
   7) deethanizing said methane-depleted product stream in a deethanizer from which a $C_2$–product stream is taken as overhead and a $C_3$+product stream is taken as bottoms; and which process further comprises:
   contacting at least one of said product streams from steps 2 through 7 with a metal oxide-containing catalyst in the presence of a $C_1$ to $C_6$ alcohol under conditions sufficient to convert said oxygenate impurities selected from aldehyde and/or ketone to an olefin and/or oxygenate of higher carbon number than said aldehyde and/or ketone.

2. The process of claim 1 wherein said contacting is carried out with said compressed and cooled product stream.

3. The process of claim 1 wherein said contacting is carried out with said water-depleted product stream.

4. The process of claim 1 wherein said contacting is carried out with said carbon dioxide-depleted product stream.

5. The process of claim 1 wherein said contacting is carried out with said dried product stream.

6. The process of claim 1 wherein said contacting is carried out with said methane-depleted product stream.

7. The process of claim 1 wherein said contacting is carried out with said $C_2$–product stream.

8. The process of claim 1 wherein said contacting is carried out with said $C_3$+product stream.

9. The process of claim 1 wherein said aldehyde is selected from $C_2$ to $C_5$ aldehyde and said ketone is selected from $C_3$ to $C_6$ ketone and said metal oxide-containing catalyst comprises an oxide of a metal selected from the group consisting of Group 2 metals, Group 3 metals, and Group 4 metals.

10. The process of claim 1 wherein said $C_1$ to $C_6$ alcohol is methanol.

11. The process of claim 1 wherein said metal oxide-containing catalyst comprises an oxide of a metal selected from the group consisting of Mg, Ca, Sr, Ba and Ra.

12. The process of claim 1 wherein said metal oxide-containing catalyst comprises an oxide of a metal selected from the group consisting of Sc, Y, La, Ge, Pr, Nd, Pin, Sm, Eu, Gd, Tb, Dy, Ho, Er, Tm, Yb, Lu, Ac, Th, Pa, U, Np, Pu, Am, Cm, Bk, Cf, Es, Fm, Md, No, and Lr.

13. The process of claim 1 wherein said metal oxide-containing catalyst comprises an oxide of a metal selected from the group consisting of Sc, Y, La, and Ce.

14. The process of claim 1 wherein said metal oxide-containing catalyst comprises an oxide of Y.

15. The process of claim 1 wherein said metal oxide-containing catalyst comprises an oxide of a metal selected from the group consisting of Ti, Zr, and Hf.

16. The process of claim 1 wherein said metal oxide-containing catalyst comprises an oxide of Zr.

* * * * *